United States Patent

Kokish et al.

[11] Patent Number: 6,165,202
[45] Date of Patent: Dec. 26, 2000

[54] ABSORBABLE POLYMERS AND SURGICAL ARTICLES FABRICATED THEREFROM

[75] Inventors: Lydmilla K. Kokish, Los Gatos, Calif.; Rooma M. Mehta, Branford, Conn.; Mark S. Roby, Killingworth, Conn.; Jerry Y. Jonn, North Haven, Conn.

[73] Assignee: United States Surgical Corporation, Norwalk, Conn.

[21] Appl. No.: 09/326,926

[22] Filed: Jun. 5, 1999

Related U.S. Application Data

[60] Provisional application No. 60/107,634, Nov. 9, 1998, and provisional application No. 60/091,865, Jul. 6, 1998.

[51] Int. Cl.[7] ................................................. A61B 17/04
[52] U.S. Cl. ............................................................ 606/230
[58] Field of Search ....................... 606/230, 231; 258/354

[56] References Cited

U.S. PATENT DOCUMENTS

| | | | |
|---|---|---|---|
| 4,045,418 | 8/1977 | Sinclair | 260/78.3 |
| 4,052,988 | 10/1977 | Doddi et al. | 128/335.5 |
| 4,057,537 | 11/1977 | Sinclair | 260/78.3 R |
| 4,243,775 | 1/1981 | Rosensaft et al. | 225/415 |
| 4,300,565 | 11/1981 | Rosensaft et al. | 128/335.5 |
| 4,605,730 | 8/1986 | Shalaby et al. | 528/357 |
| 4,643,191 | 2/1987 | Bezwada et al. | 128/335.5 |
| 4,653,497 | 3/1987 | Bezwada et al. | 128/335.5 |
| 4,700,704 | 10/1987 | Jamiolkowski et al. | 128/335.5 |
| 4,838,267 | 6/1989 | Jamiolkowski et al. | 128/335.5 |
| 4,891,263 | 1/1990 | Kotliar et al. | 428/225 |
| 4,916,193 | 4/1990 | Tang et al. | 525/413 |
| 4,916,207 | 4/1990 | Boyle et al. | 528/413 |
| 4,920,203 | 4/1990 | Tang et al. | 252/409 |
| 4,994,074 | 2/1991 | Bezwada et al. | 606/230 |
| 5,047,048 | 9/1991 | Bezwada et al. | 606/231 |
| 5,076,807 | 12/1991 | Bezwada et al. | 606/230 |
| 5,133,739 | 7/1992 | Bezwada et al. | 606/230 |
| 5,225,520 | 7/1993 | Kennedy et al. | 528/354 |
| 5,236,444 | 8/1993 | Muth et al. | 606/230 |
| 5,274,074 | 12/1993 | Tang et al. | 528/370 |
| 5,403,347 | 4/1995 | Roby et al. | 606/230 |
| 5,468,253 | 11/1995 | Bezwada et al. | 606/230 |
| 5,522,841 | 6/1996 | Roby et al. | 606/230 |
| 5,554,170 | 9/1996 | Roby et al. | 606/230 |
| 5,713,920 | 2/1998 | Bezwada et al. | 606/230 |
| 5,718,716 | 2/1998 | Goddard et al. | 606/230 |
| 5,854,383 | 12/1998 | Erneta et al. | 528/354 |
| 6,031,018 | 2/2000 | Scopelianos et al. | 523/105 |

FOREIGN PATENT DOCUMENTS

0261470 A1  9/1987  European Pat. Off. ............. 606/230

OTHER PUBLICATIONS

Sawhney et al. "Rapidly Degraded Terpolymers of Racemic Lactide Glycolide and Epsilon Caprolactone with increased Hydrophilicity by Copolymerization with Polyethers" 1990, vol. 24 pp. 1397–1411.

Gu et al. "Biodegradable block copolymer matrices for long–acting contraceptives with constant release." vol. 22(1), pp. 3–14, 1992.

*Primary Examiner*—Michael Buiz
*Assistant Examiner*—Tan-Uyen T. Ho

[57] ABSTRACT

Synthetic absorbable medical devices made totally or in part from a random polymer comprising glycolide, lactde and caprolactone are provided. The polymer can be fabricated into a monofilament which exhibits physical characteristics equivalent to or superior than gut sutures.

19 Claims, 2 Drawing Sheets

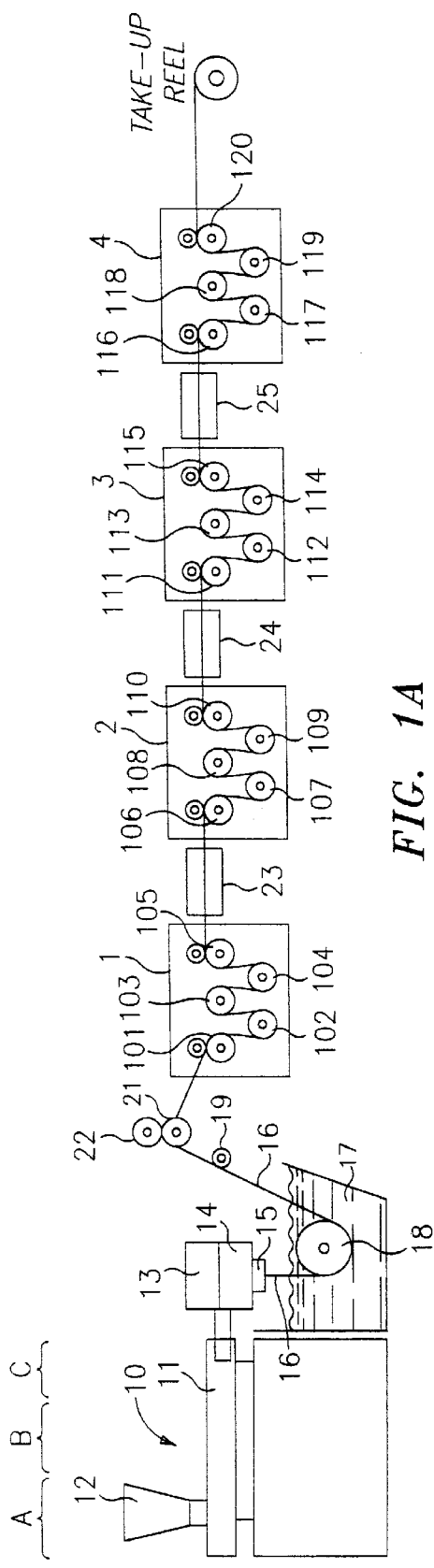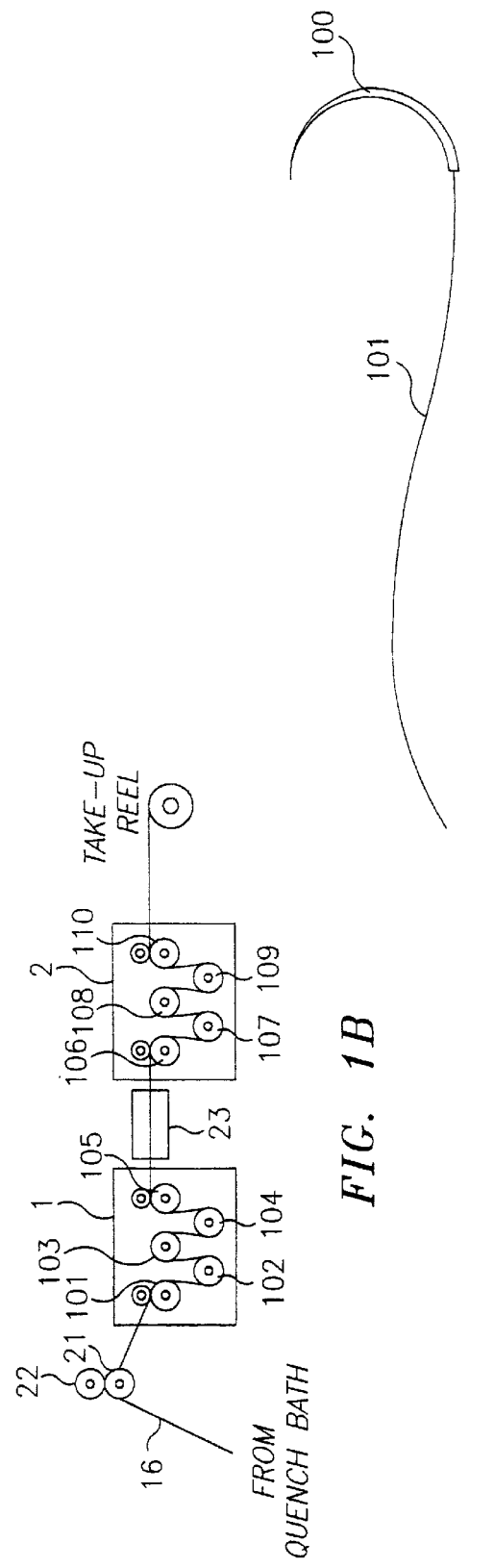

ABSORBABLE POLYMERS AND SURGICAL ARTICLES FABRICATED THEREFROM

This application claims benefit to Provisional Application 60/107,634 filed Nov. 9, 1998 which claims benefit to Provisional Application 60/091,865 filed Jul. 6, 1998.

TECHNICAL FIELD

Absorbable terpolymers of randomly polymerized glycolide, lactide and caprolactone are described. Processes for making the terpolymers and surgical articles made totally or in part from such terpolymers, including sutures, are also described.

BACKGROUND

Bioabsorbable surgical devices made from copolymers derived from glycolide and epsilon-caprolactone are known in the art. Such bioabsorbable surgical devices include surgical sutures.

A desirable characteristic of a bioabsorbable suture is its ability to exhibit and maintain desired tensile properties for a predetermined time period followed by rapid absorption of the suture mass (hereinafter "mass loss".)

Synthetic absorbable sutures are known in the art. Absorbable multifilament sutures such as DEXON II sutures (made from glycolide homopolymer and commercially available from United States Surgical Corporation, North Haven, Conn.), VICRYL sutures (made from a copolymer of glycolide and lactide and commercially available from Ethicon, Inc., Sommerville, N.J.), and POLYSORB sutures (also made from a copolymer of glycolide and lactide and commercially available from United States Surgical Corporation, North Haven, Conn.) are known in the industry as short term absorbable sutures. The classification short term absorbable sutures generally refers to surgical sutures which retain at least about 20 percent of their original strength at three weeks after implantation, with the suture mass being essentially absorbed in the body within about 60 to 90 days post implantation.

Long term absorbable sutures are generally classified as sutures capable of retaining at least about 20 percent of their original strength for six or more weeks after implantation, with the suture mass being essentially absorbed in the body within about 180 days post implantation. For example, PDS II sutures (commercially available from Ethicon, Inc., Sommerville, N.J.), are synthetic absorbable monofilament sutures that reportedly retain at least about 20 to 30 percent of its original strength six weeks after implantation. However, PDS II reportedly exhibits minimal mass loss until 90 days after implantation with the suture mass being essentially absorbed in the body about 180 days after implantation. MAXON suture (commercially available from United States Surgical Corporation, North Haven, Conn.) is another absorbable synthetic monofilament that reportedly generally fits this absorption profile.

Most recently, United States Surgical Corporation has introduced BIOSYN monofilament sutures which exhibit good flexibility, handling characteristics, knot strength and absorption characteristics similar to those of presently available short term absorbable multifilament sutures.

Another attempt to provide an acceptable synthetic absorbable monofilament sutures resulted in MONOCRYL, a suture fabricated from an absorbable block copolymer containg glycolide and epsilon-caprolactone, commercially available from Ethicon, Inc.

However, no synthetic absorbable monofilament sutures exist today which approximate the strength retention, mass loss, and modulus of sutures commonly referred to in the art as "catgut" or "gut" sutures. It is well known in the art that the term gut suture refers to a collagen based suture of any type or origin often fabricated from the mammalian intestines, such as the serosal layer of bovine intestines or the submucosal fibrous layer of sheep intestines. Gut sutures exhibit the unique combination of two week strength retention and about 75 day mass loss while maintaining acceptable modulus and tensile strength; and thus are still widely used in gynecological surgery.

It would be advantageous to provide a synthetic absorbable suture which exhibits physical properties similar to the gut suture.

U.S. Pat. No. 4,700,704 to Jamiolkowski does teach that sutures can be fabricated from random copolymers of glycolide and epsilon-caprolactone, and more specifically from random copolymers containing from 20 to 35 weight percent epsilon-caprolactone and from 65 to 80 weight percent glycolide. Moreover, Jamiolkowski reports that sutures fabricated from glycolide/epsilon-caprolactone copolymers containing over 35% caprolactone are not orientable to a dimensionally stable fiber. Jamiolkowski further reports that some sutures fabricated from glycolide/epsilon-caprolactone copolymers containing 15% caprolactone are also not orientable to a dimensionally stable fiber. Furthermore, Jamiolkowski also reports the undesirable combination of low modulus and low tensile strength for the glycolide/epsilon-caprolactone copolymers which he was able to fabricate into sutures.

U.S. Pat. Nos. 4,045,418 and 4,057,537 disclose random copolymers obtained by copolymerizing lactide and epsilon-caprolactone as well as terpolymers obtained by polymerizing lactide, epsilon-caprolactone, and glycolide. The copolymers as well as the terpolymers disclosed in U.S. Pat. Nos. 4,045,418 and 4,057,537 have at least 60% by weight lactide. These copolymers have been described in the literature as having "one major drawback which has prevented their wide spread use. Although the copolymers can be literally interpreted to be 'bioabsorbable', the rate of absorption is so slow that it renders the copolymers practically useless for numerous medical applications" (see U.S. Pat. No. 5,468,253 at column 2, lines 24 et seq.). In fact, U.S. Pat. No. 5,468,253 addresses this problem by disclosing medical devices formed from a random copolymer of: a) from about 30 to about 50 weight percent of epsilon-caprolactone, trimethylene carbonate, an ether lactone and combinations thereof, and b) the balance being substantially glycolide or para-dioxanone.

Therefore, it would be unexpected that medical devices such as sutures made from random copolymer of glycolide, epsilon-caprolactone, and lactide would provide the strength retention and mass loss characteristics approximating those of gut sutures while maintaining an acceptable modulus and tensile strength.

SUMMARY

It has now surprisingly been found that absorbable surgical articles formed from a random terpolymer of glycolide caprolactone and lactide exhibit strength retention, mass loss and modulus similar to that of gut sutures. Preferably, the terpolymers used in forming surgical articles include between about 14 and about 17 weight percent of units derived from caprolactone, between about 70 and 76 weight percent of units derived from glycolide, and between about 9 to about 15 weight percent of units derived from lactide.

In particularly useful embodiments, the random terpolymers can be spun into fibers. The fibers can be advantageously fabricated into either monofilament or multifilament sutures having physical properties similar to those of gut sutures.

In addition, a process of making such synthetic absorbable monofilament sutures from the above described caprolactone/glycolide/lactide random terpolymers has been found. The process, for a given size suture, comprises the operations of extruding the random caprolactone/glycolide/lactide copolymer at an extrusion temperature of from about 130° C. to about 190° C. to provide a monofilament fiber, passing the solidified monofilament through water (or other suitable liquid medium) quench bath at a temperature of from about 15° C. to about 28° C. or through in air (or other suitable gaseous medium) at from about 15° C. to about 30° C., stretching the monofilament through a series of air ovens at an overall stretch ratio of from about 6:1 to about 13:1 to provide a stretched monofilament. In a particularly useful embodiment, the monofilament is stretched through three air ovens by four godet stations. The first air oven is maintained at ambient temperature, whereas the second air oven is heated to a temperature above the crystalization temperature of the glycolide/lactide/epsilon-caprolactone copolymer at about 80° C. to about 115° C., and the third air oven is set at about 80° C. to about 125° C. The draw ratio between the first and second godet station ranges between about 5:1 to about 12:1. The draw ratio between the second and third godet station ranges between about 1.1:1 to about 2.6:1. The draw ratio between the third and fourth godet station ranges between about 0.75:1 to about 1.05:1. The suture then may be annealed with or without relaxation at a temperature of from about 80° C. to about 125° C. to provide the finished suture.

BRIEF DESCRIPTION OF THE DRAWINGS

FIG. 1A is a schematic illustration of an apparatus which is suitable for manufacturing of monofilament sutures disclosed herein;

FIG. 1B is a modificatiuon of the apparatus shown in FIG. 1A which is particularity suitable for manufacturing monfilament sutures of smaller size; e.g. sizes 4/0 and smaller.

FIG. 2 is a perspective view of a suture attached to a needle.

DESCRIPTION OF THE PREFERRED EMBODIMENTS

Figure 3A:
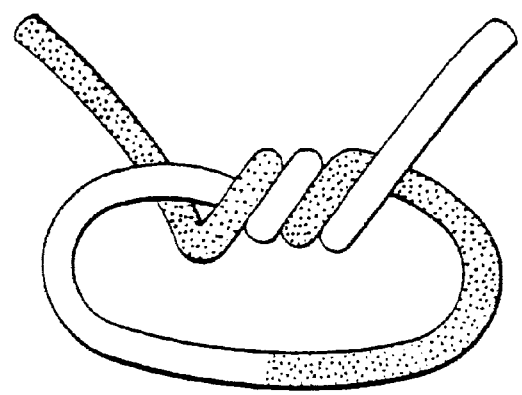
FIG. 3A–3C illustrate the formation of the knot which was employed in the loop pull test used in Table IV.

It has been found that glycolide, epsilon-caprolactone, and lactide monomers can advantageously be combined to form a random polymer useful in forming surgical articles having strength retention, mass loss, and modulus characteristics similar to or superior to gut sutures.

The random polymer can be prepared using conventional techniques. For example, monomers can be dried, mixed in a reaction vessel with an initiator (either a single or multifunctional initiator) and a suitable polymerization catalyst and polymerized at temperatures from about 170° C. to about 200° C. for a period of time ranging from about 10 hours to about 30 hours.

The polymer has randomly combined repeating units derived from glycolide, lactide and epsilon-caprolactone. Repeating units derived from glycolide comprise between about 70 and about 76 weight percent of the polymer, while repeating units derived from lactide comprise about 9 to about 15 weight percent of the polymer and units derived from caprolactone comprise about 14 to about 17 weight percent of polymer. Polymers of caprolactone, glycolide, and lactide having an inherent viscosity of from about 0.9 to about 1.8 dl/g measured at 30° C. and at a concentration of 0.25 g/dl in chloroform or HFIP may generally be used.

The random polymers provided herein can be blended or copolymerized with other known absorbable polymers and/or coploymers derived from materials such as glycolide, lactide, caprolactone, dioxanone, trimethylene carbonate, alkylene oxides, absorbable amides and the like. It should be understood that the above list of materials with which the random copolymer can be either blended or copolymerized is provided for illustrative purposes and is not to be construed as limiting.

The random polymers can be formed into surgical articles using any known technique, such as, for example, extrusion, molding and/or solvent casting. The copolymers can be used alone, blended with other absorbable compositions, or in combination with non-absorbable components. A wide variety of surgical articles can be manufactured from the copolymers described herein. These include but are not limited to clips and other fasteners, staples, sutures, pins, screws, prosthetic devices, wound dressings, drug delivery devices, anastomosis rings, and other implantable devices. Fibers made from the copolymers can be knitted, woven or made into non-woven materials with other fibers, either absorbable or nonabsorbable to form fabrics, such as meshes and felts. Compositions including these random copolymers can also be used as an absorbable coating for surgical devices. Preferably, however, the polymers are spun into fibers to be used in making sutures.

Multifilament sutures of the present invention may be made by methods known in the art. Braid constructions such as those disclosed and claimed in U.S. Pat. Nos. 5,059,213 and 5,019,093 are suitable for the multifilament suture of the present invention.

FIG. 1A substantially illustrates the extruding, quenching and stretching operations of the monofilament manufacturing operation herein. Extruder unit 10 is of a known or conventional type and is equipped with controls for regulating the temperature of barrel 11 in various zones thereof, e.g., progressively higher temperatures in three consecutive zones A, B and C along the length of the barrel. Pellets or powder of resins of the present invention are introduced to the extruder through hopper 12. Any of the above described polymers which are useful for the formation of fibers can be used herein.

Motor-driven metering pump 13 delivers melt extruded resin at a constant rate to spin pack 14 and thereafter through spinneret 15 possessing one or more orifices of desired diameter to provide a molten monofilament 16 which then enters quench bath 17, e.g., containing water, where the monofilament solidifies. The distance monofilament 16 travels after emerging from spinneret 15 to the point where it enters quench bath 17, i.e., the air gap, can vary and can advantageously be from about 0.5 to about 100 cm and preferably from about 1 to about 20 cm. If desired, a chimney (not shown), or shield, can be provided to isolate monofilament 16 from contact with air currents which might otherwise affect the cooling of the monofilament in an unpredictable manner. In general, barrel zone A of the extruder can be maintained at a temperature of from about 130° C. to 180° C., zone B at from about 135° C. to 190° C. and zone C at from about 135° C. to about 190° C.

Additional temperature parameters include: metering pump block 13 at from about 135° C. to about 190° C., spinneret 15 at from about 140° C. to about 190° C. and quench bath at from about 15° C. to about 25° C.

Monofilament 16 is passed through quench bath 17 around driven roller 18 and over idle roller 19. Optionally, a wiper (not shown) may remove excess water from the monofilament as it is removed from quench bath 17. On exiting the quench bath the monofilament is passed through first godet station 1, which is equiped with five individual godets, i.e. godets 101, 102, 103, 104 and 105. Upon entering godet station 1, monofilament 16 is wrapped around a first godet 101 provided with nip roll 22 to prevent slippage which might otherwise result from the subsequent stretching operation; and subsequently passed over godet 101, under godet 102, over godet 103, under godet 104, and over godet 105 to godet station 2, containing godets 106, 107, 108, 109, and 110, where it is wrapped over godet 106, under godet 107, over godet 108, under godet 109, and over godet 110. Monofilament 16 passing from godet station 1 to godet station 2 is drawn through air oven 23 at a temperature ranging form about 25° C. to about 40° C. by the godets of godet station 2 which rotate at speeds faster than the speed of the godet station 1 to provide the desired draw ratio, which is from about 5:1 to about 12:1 and preferably from about 6:1 to about 10:1, to effect the molecular orientation of the copolymer from which it is fabricated and thereby increase its tensile strength.

Following the initial draw at about 20° C. to about 40° C. temperature, monofilament 16 is then subjected to a second and a third drawing operation. Monofilament 16 is subsequently drawn from godet 110 through air oven 24, which is maintained at from about 80° C. to about 115° C., to godet station 3 containing godets 111, 112, 113, 114, and 115 where it is wrapped over godet 111, under godet 112, over godet 113, under godet 114, and over godet 115. Godet station 3 spins faster than godet station 2 to provide the desired draw ratio, which is from about 1.3:1 to about 2.6:1. Monofilament 16 is then drawn from godet 115 through air oven 25, which is maintained at from about 80° C. to about 125° C., by godet station 4, containing godets 116, 117 118, 119, and 120 where it is wrapped over godet 116, under godet 117, over godet 118, under godet 119, and over godet 120. Godet station 4 spins faster than godet station 3 to provide the desired draw ratio, which is from about 0.75:1 to about 1.05:1. It should be understood that the godet arrangements in each of godet stations 1, 2, 3, and 4, respectively should not be limited to the above described arrangement and that each godet station may have any suitable godet arrangement.

In an alternative operation for sutures for smaller size sutures, e.g. sizes 4/0 to 8/0, as shown in FIG. 1B monofilament 16 is only passed through godet stations 1 and 2 and not subjected to any further stetching operations.

Annealing of the suture also may be accomplished with or without shrinkage of the suture. In carrying out the annealing operation, the desired length of suture may be wound around a creel and the creel placed in a heating cabinet under nitrogen flow maintained at the desired temperature, e.g. about 80° C. to about 125° C., as described in U.S. Pat. No. 3,630,205. After a suitable period of residency in the heating cabinet, e.g., for up to about 18 hours or so, the suture will have undergone essentially no shrinkage. As shown in U.S. Pat. No. 3,630,205, the creel may be rotated within the heating cabinet in order to insure uniform heating of the monofilament or the cabinet may be of the circulating hot air type in which case uniform heating of the monofilament will be achieved without the need to rotate the creel. Thereafter, the creel with its annealed suture is removed from the heating cabinet and when returned to room temperature, the suture is removed from the creel, conveniently by cutting the wound monofilament at opposite ends of the creel. The annealed sutures, optionally attached to surgical needles, are then ready to be packaged and sterilized.

Alternatively, the suture may be annealed on line with or without relaxation. For relaxation, the fourth godet station rotates at a slower speed than the third godet station thus relieving tension on the filament.

The suture disclosed herein, suture 101, may be attached to a surgical needle 100 as shown in FIG. 2 by methods well known in the art. Wounds may be sutured by passing the needled suture through tissue to create wound closure. The needle preferably is then removed from the suture and the suture tied.

It is further within the scope of this invention to incorporate one or more medico-surgically useful substances into the presently disclosed polymers and surgical articles, e.g., those medico-surgically useful substances which accelerate or beneficially modify the healing process when particles are applied to a surgical repair site. So, for example, the suture can carry a therapeutic agent which will be deposited at the repair site. The therapeutic agent can be chosen for its antimicrobial properties, capability for promoting repair or reconstruction and/or new tissue growth. Antimicrobial agents such as broad spectrum antibiotic (gentamycin sulfate, erythromycin or derivatized glycopeptides) which are slowly released into the tissue can be applied in this manner to aid in combating clinical and sub-clinical infections in a tissue repair site. To promote repair and/or tissue growth, one or several growth promoting factors can be introduced into the sutures, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system.

It is contemplated that it may be desirable to dye the sutures in order to increase visibility of the suture in the surgical field. Dyes known to be suitable for incorporation in sutures can be used. Such dyes include but are not limited to carbon black, bone black, D&C Green No. 6, and D&C Violet No. 2 as described in the handbook of U.S. Colorants for Food, Drugs and Cosmetics by Daniel M. Marrion (1979). Preferably, sutures in accordance with the invention are dyed by adding up to about a few percent and preferably about 0.2% dye, such as D&C Violet No. 2 to the resin prior to extrusion, although addition of the dye during polymerization is also suitable.

In order that those skilled in the art may be better able to practice the compositions and methods described herein, the following examples are given as an illustration of the preparation of random polymers as well as of the preparation and superior characteristics of sutures made from the random copolymers. It should be noted that the invention is not limited to the specific details embodied in the examples and further that all ratios or parts recited are by weight, unless otherwise indicated.

EXAMPLE 1

Dry glycolide (1320 grams), dry 1-lactide (300 grams), and distilled epsilon-caprolactone (380 grams) were added to a reactor along with 0.24 grams of distilled stannous octoate and 0.2 grams of distilled diethylene glycol (DEG). The mixture was dried for about 21 hours and 40 minutes with agitation under flow of nitrogen. The reactor temperature was then set at 100° C. When the temperature of the reaction vessel reached 100° C., the temperature was maintained for about 15 minutes. Then the temperature of the reaction vessel was raised to 150° C. and then the reaction vessel heated for about an additional 15 minutes. The temperature of the reaction was then raised to about 190° C. and polymerization conducted with stirring under a nitrogen atmosphere for about 25 hours and 40 minutes.

The reaction product is then isolated, comminuted, and treated to remove residual reactants using known techniques. The treatment to remove residual reactants occurs at 100° C. for 48 hours under vacuum. NMR analysis, using a commercially available Bruker NMR, model number DPX-300, revealed the resultant polymer contained 12.9 weight percent lactide, 16.6 weight percent caprolactone, and 70.5 weight percent glycolide.

EXAMPLE 2

Dry glycolide (4080 grams), dry 1-lactide (900 grams), and distilled epsilon-caprolactone (1020 grams) were added to a reactor along with 0.72 grams of distilled stannous octoate and 1.2 grams of distilled diethylene glycol (DEG). The mixture was dried for about 18.75 hours with agitation under flow of nitrogen. The reactor temperature was then set at 100° C. When the temperature of the reaction vessel reached 100° C., the temperature was maintained for about 15 minutes. Then the temperature of the reaction vessel was raised to 150° C. and then the reaction vessel heated for about an additional 15 minutes. The temperature of the reaction vessel was then raised to about 190° C. and polymerization conducted with stirring under a nitrogen atmosphere for about 23 hours and 10 minutes.

The reaction product is then isolated, comminuted, and treated to remove residual reactants using known techniques. The treatment to remove residual reactants occurs at 90° C. for 48 hours under vaccuum. NMR analysis, using a commercially available Bruker NMR, model number DPX-300, revealed the resultant polymer contained 12.5 weight percent lactide, 15.3 weight percent caprolactone, and 72.2 weight percent glycolide.

EXAMPLE 3

Dry glycolide (3960 grams), dry 1-lactide (1020 grams), and distilled epsilon-caprolactone (1020 grams) were added to a reactor along with 0.72 grams of distilled stannous octoate and 0.6 grams of distilled diethylene glycol (DEG). The mixture was dried for about 10 hours with agitation under flow of nitrogen. The reactor temperature was then set at 100° C. When the temperature of the reaction vessel reached 100° C., the temperature was maintained for about 15 minutes. Then the temperature of the reaction vessel was raised to 150° C. and the reaction vessel heated for about an additional 15 minutes. The temperature of the reactants was then raised to about 190° C. and polymerization conducted with stirring under a nitrogen atmosphere for about 22 hours and 35 minutes.

The reaction product is then isolated, comminuted, and treated to remove residual reactants using known techniques. The treatment to remove residual reactants occurs at 90° C. for 48 hours under vacuum. NMR analysis, using a commercially available Bruker NMR, model number DPX-300, revealed the resultant polymer contained 14.5 weight percent lactide, 14.9 weight percent caprolactone, and 70.6 weight percent glycolide.

EXAMPLE 4

Dry glycolide (4200 grams), dry 1-lactide (780 grams), and distilled epsilon-caprolactone (1020 grams) were added to a reactor along with 0.72 grams of distilled stannous octoate and 0.6 grams of distilled diethylene glycol (DEG). The mixture was dried for about 5.75 hours with agitation under flow of nitrogen. The reactor temperature was then set at 100° C. When the temperature of the reaction vessel reached 100° C. the temperature was maintained for about 15 minutes. Then the temperature of the reaction vessel was raised to about 150° C. and then the reaction vessel heated for about an additional 15 minutes. The temperature of the reaction vessel was then raised to about 190° C. and polymerization conducted with stirring under a nitrogen atmosphere for about 23 hours and 15 minutes.

The reaction product is then isolated, comminuted, and treated to remove residual reactants using known techniques. The treatment to remove residual reactants occurs at 90° C. for 48 hours under vacuum. NMR analysis, using a commercially available Bruker NMR, model number DPX-300, revealed the resultant polymer contained 11.2 weight percent lactide, 14.2 weight percent caprolactone, and 74.6 weight percent glycolide.

Table I below sets forth typical conditions for extruding, stretching of size 3/0 sutures. All of the monofilament sutures were fabricated from the resins of Examples 1–4, respectively.

TABLE I

CONDITIONS OF MANUFACTURING VARIOUS SIZES OF MONOFILAMENT OF THE PRESENT INVENTION

| Example | 1 | 2 | 3 | 4 |
| --- | --- | --- | --- | --- |
| Suture Size | 3/0 | 3/0 | 3/0 | 3/0 |
| Process Conditions | EXTRUSION | | | |
| extruder screw, rpm | 4.6 | 3.0 | 2.1 | 3.8 |
| pump, rpm | 10.9 | 7.8 | 6.0 | 5.1 |
| driven roller, mpm | 2.21 | 0 | 0 | 0 |
| barrel temp., ° C., zone A | 143 | 137 | 136 | 150 |
| barrel temp., ° C., zone B | 146 | 143 | 140 | 155 |
| barrel temp., ° C., zone C | 150 | 143 | 144 | 156 |
| clamp temp., ° C., | 151 | 143 | 140 | 155 |
| adapter temp., ° C. | 151 | 144 | 143 | 158 |
| spinneret temp., ° C. | 151 | 149 | 148 | 162 |
| block temp., ° C. | 151 | 146 | 140 | 160 |
| barrel melt temp., ° C. | 165 | 160 | 156 | 173 |
| pump melt temp., ° C. | 157 | 149 | 143 | 163 |
| spinneret melt temp., ° C. | N/A | 158 | 155 | 174 |
| barrel pressure, psi | 1060 | 550 | 580 | 520 |
| pump pressure, psi | 1000 | 500 | 500 | 500 |
| spinneret pressure, psi | 1480 | 470 | 810 | 430 |
| pump size, cc per revolution | 0.16 | 0.16 | 0.16 | 0.16 |
| diameter of spinneret, orifices, mm | 1.2 | 1.2 | 1.2 | 1.2 |
| no. of spinneret orifices | 1 | 1 | 1 | 1 |
| quench bath temp., ° C. | 25 | 25 | 25 | 25 |
| Stretching (Orienting) Operation | | | | |
| draw bath temp., ° C. | N/A | N/A | N/A | N/A |
| first godet station, mpm | 2.34 | 1.5 | 1.2 | 1.2 |
| second godet, mpm | 15.8 | 12.2 | 9.6 | 9.1 |
| third godet station, mpm | 23.0 | 16.5 | 13.1 | 11.9 |
| fourth godet station, mpm | 19.0 | 15.2 | 11.7 | 9.5 |
| first oven temp, ° C. | 40 | 38 | 38 | 38 |
| second oven temp, ° C. | 85 | 109 | 92 | 108 |
| third oven temp, ° C. | 105 | 105 | 98 | 110 |
| overall draw ratio | 9.82:1 | 11:1 | 10.92:1 | 9.9:1 |
| Relaxation | 17% | 10.7% | 10% | 20% |

TABLE I-continued

CONDITIONS OF MANUFACTURING VARIOUS SIZES
OF MONOFILAMENT OF THE PRESENT INVENTION

| Example | 1 | 2 | 3 | 4 |
|---|---|---|---|---|
| Annealing Operation | | | | |
| annealing temp., °C. | 105 | 110 | 100 | 110 |
| time (hrs.) | 6 | 6 | 6 | 6 |

The physical properties of the sutures and the procedures employed for their measurement are set forth in Table II as follows:

TABLE II

PROCEDURES FOR MEASURING PHYSICAL PROPERTIES
OF MONOFILAMENT SUTURES OF THE PRESENT INVENTION

| Physical Property | Test Procedure |
|---|---|
| knot-pull strength, kg | U.S.P. XXI, tensile strength, sutures (881) |
| straight-pull strength, kg | ASTM D-2256, Instron Corporation |
| elongation, % | ASTM D-2256 |
| tensile strength, kg/mm$^2$ | ASTM D-2256, Instron Corporation Series IX Automated Materials Testing System 1.03A |
| Young's Modulus | Instron Merlin Software version 2000 Series IX calculation 18.3 (commercially available from Instron Corporation) |

Table III below sets forth the physical properties of the size 3/0 suture of the present invention.

TABLE III

| Physical Property | Example 1 | Example 2 | Example 3 | Example 4 |
|---|---|---|---|---|
| diameter (mm) | .324 | 0.316 | .319 | .319 |
| knot-pull strength (kg) | 2.64 | 2.51 | 2.29 | 2.99 |
| Young's Modulus (kpsi) | 380 | 661 | 523 | 734 |
| Elongation % | 38 | 19 | 27 | 29 |
| Tensile Strength (kpsi) | 64.3 | 81.8 | 73.9 | 94.5 |

As the data in Tables III illustrates, the suture made of the copolymer provided herein shows a desired physical properties, such as modulus and tensile strength.

INVITRO STRENGTH RETENTION

Figure 3B:
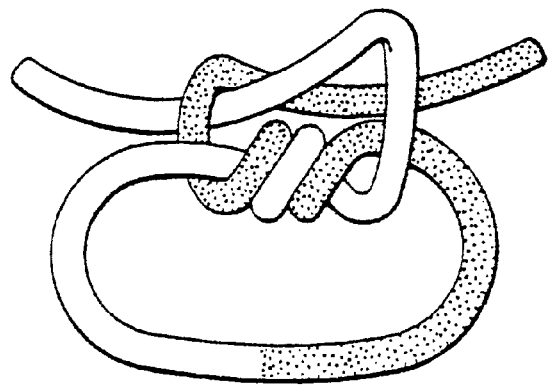
Figure 3C:
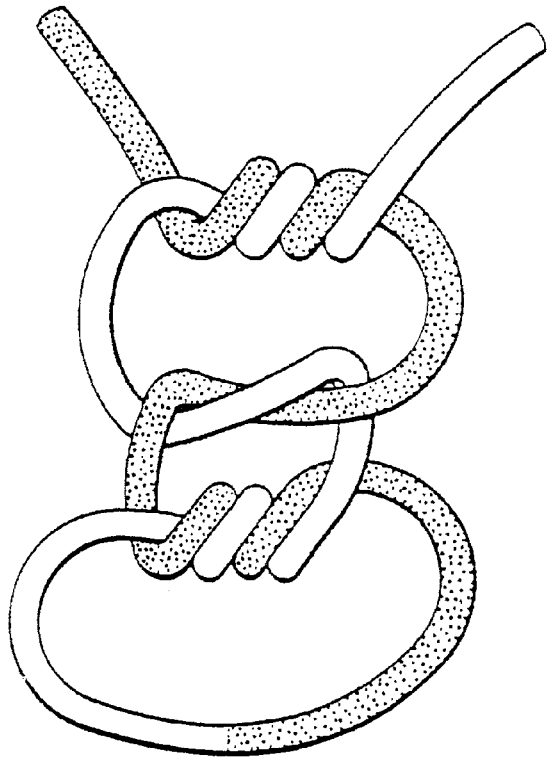

Monofilament sutures manufactured in accordance with the above described process using the copolymer of Example 1 were tested for in vitro strength retention. In vitro loop-pull strength retention is indicative of in vivo strength retention. The in vitro strength retention of the suture was tested as follows:

To simulate in vivo conditions, the suture samples were stored in a container filled with Sorenson's buffer solution at 37° C. After various periods of time, the suture samples were then removed from the container to test their loop-pull strength as follows. A knotted loop was formed in a test suture in three steps as shown in FIGS. 3A–3C. As shown in step 1 of FIG. 3A, each suture was given a double throw (left over right) around a 2 cm diameter cylinder. In Step 2, the free ends of the suture were set in a single throw (right over left) onto the initial throw of step 1. Finally, in step 3, another double throw (left over right) was set onto the single throw of Step 2 to complete the knot. The free ends of the suture were cut to approximately 0.5 inches and the loop was carefully eased from the cylinder.

Testing of the loop was carried out using an Instron Tensile Tester Model No. 4307 (commercially available from Instron Corporation, Canton, Mass.), operated with a crosshead speed of 51 mm/min and equipped with flat grips, each having a pin over which the loop is positioned.

The results of the tests are presented in Table IV hereinbelow. In the strength retention data reported in Table IV, $T_n$ represents the time elapsed in weeks since the sample was placed in the solution, with n representing the number of weeks.

TABLE IV

PERCENTAGE OF IN VITRO STRENGTH RETAINED

| COMPOSITION | $T_1$ | $T_2$ | $T_3$ |
|---|---|---|---|
| EXAMPLE 1 | 23 | 15 | 0 |
| EXAMPLE 2 | 34 | 3 | 0 |
| EXAMPLE 3 | 32 | 0 | 0 |
| MONOCRYL | 58 | 26 | 3 |

IN VITRO MASS LOSS

Monofilament sutures manufactured in accordance with the above described process using the polymer of Examples 1–4 were tested for in vitro mass retention. In vitro mass retention strength is indicative of in vivo mass retention. The in vitro strength retention of the suture was tested as follows:

To simulate in vivo conditions, the suture samples were weighed and stored in a fritted microencapsulation thimble (commercially available from Chemglass, Inc., Vineland, N.J.), which was placed in a scintillation vial filled with Sorenson's buffer solution. The scintillation vials were then placed in a water bath at 80° C. After various periods of time, the microextraction thimbles containing the suture samples were then removed from the scintillation vial, vacuum filtered, rinsed with distilled water, vacuum filtered, and dried for about 6 hours at about 40° C. under vacuum and subsequently the suture and thimble were weighed. The weight of the suture remaining was calculated by substracting the weight of the thimble from the weight of the thimble containing the remaining suture. The percentage of the suture retained was calculated by dividing the weight of the remaining suture by the original weight of the suture and multiplying the result by 100.

The results of the tests are presented in Table V hereinbelow. In the mass retention data reported in Table V, $T_n$ represents the time elapsed in hours since the sample was placed in the solution, with n representing the number of hours. It is well known in the art that one hour of immersion in the container filled with Sorenson's buffer solution at 80° C. approximates about one day of invivo mass loss. For comparison purposes, the same tests were conducted on Monocryl sutures. All comparative tests were performed on size 3/0 sutures.

TABLE V

| COMPO-SITION Time (hr) | $T_1$ 8 | $T_2$ 24 | $T_3$ 32 | $T_4$ 48 | $T_6$ 56 | $T_8$ 72 | $T_{10}$ 96 | $T_{12}$ 120 |
|---|---|---|---|---|---|---|---|---|
| PERCENTAGE OF IN VITRO MASS RETAINED | | | | | | | | |
| EXAMPLE 1 | 90.52 | 42.58 | 35.35 | 25.54 | 23.50 | 19.56 | 12.94 | 11.43 |
| EXAMPLE 2 | 88.32 | 43.96 | 33.77 | 24.83 | 22.63 | 18.7 | 14.76 | 11.72 |
| EXAMPLE 3 | 92.05 | 40.91 | 28.26 | 21.56 | 18.36 | 15.0 | 12.71 | 8.73 |
| EXAMPLE 4 | 89.28 | 54.15 | 42.95 | 32.81 | 29.24 | 23.74 | 18.68 | 13.33 |
| Monocryl | 94.86 | 74.79 | 66.83 | 47.95 | 42.63 | 35.31 | 32.14 | 27.32 |

Modifications and variations of the compositions and processes disclosed herein are possible in light of the above teachings. It is therefore to be understood that changes may be made in particular embodiments described which are within the full intended scope of the invention as defined by the claims.

What is claimed is:

1. A medical device fabricated totally or in part from a random polymer comprising from about 70 to about 76 weight percent glycolide, about 14 to about 17 weight percent epsilon-caprolactone, and about 9 to about 15 weight percent lactide.

2. The medical device of claim 1 wherein the device is a surgical suture.

3. The suture of claim 2 wherein the random polymer comprises about 70.6 weight percent glycolide, about 14.9 weight percent caprolactone, and about 14.5 weight percent lactide.

4. The suture of claim 2 wherein the suture exhibits two week strength retention of about 15%, as measured in Sorenson's buffer solution at 37° C.

5. The suture of claim 2 wherein the suture exhibits a mass loss of about 91% in 96 hours as measured in Sorenson's buffer solution at 80° C.

6. The suture of claim 2 wherein the suture exhibits a modulus ranging from about 380 kpsi to about 760 kpsi.

7. The suture of claim 2 wherein the suture exhibits a knot pull strength of about 2.0 to about 3.0 kg.

8. The suture of claim 2 wherein the suture is a size 3/0 suture exhibiting a modulus of about 523 kpsi.

9. The suture of claim 1 wherein the suture is a size 3/0 suture exhibiting a knot pull strength of about 2.3 kg.

10. The suture of claim 1 wherein the suture is a size 3/0 suture exhibiting a tensile strength of about 100 kpsi.

11. The suture of claim 1 wherein the suture is a size 3/0 suture exhibiting the following characteristics:

modulus about 350 to about 750 kpsi knot pull strength about 2.2 to about 3 kg tensile strength about 64 to about 105 kpsi.

12. The medical device of claim 1 comprising a medico-surgically useful substance.

13. The suture of claim 1 wherein the random polymer possesses an inherent viscosity of about 0.9 to about 1.8 dl/g at 30° C. and at a concentration of 0.25 g/dl in HFIP.

14. The suture of claim 1 wherein the suture is a size 3/0 suture and exhibits a mass loss of about 50% after 24 hours in Sorenson's buffer solution at 80° C.

15. The suture of claim 1 wherein the suture is a size 3/0 suture and exhibits a mass loss of about 70% after 48 hours in Sorenson's buffer solution at 80° C.

16. The suture of claim 1 wherein the suture is a size 3/0 suture and exhibits a mass loss of greater than about 85% after 120 hours in Sorenson's buffer solution at 80° C.

17. The medical device of claim 1 wherein the device is a staple, clip, other fastener, pin, screw, prosthetic device, mesh, or felt.

18. The medical device of claim 1 wherein the random polymer is blended with at least one another absorbable composition.

19. The medical device of claim 1 wherein the random copolymer is copolmerized with one other absorbable composition.

* * * * *